US006489502B2

(12) United States Patent
Janke et al.

(10) Patent No.: US 6,489,502 B2
(45) Date of Patent: Dec. 3, 2002

(54) PROCESS FOR PREPARING PHOSPHORIC ACID ESTERS

(75) Inventors: Nikolaus Janke, Dormagen (DE); Manfred Pieroth, Köln (DE); Dieter Heinz, Leverkusen (DE); Werner Bäcker, Wipperfürth (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/729,542

(22) Filed: Dec. 4, 2000

(65) Prior Publication Data

US 2002/0038044 A1 Mar. 28, 2002

(30) Foreign Application Priority Data

Oct. 16, 2000 (DE) .......................................... 100 51 189
Dec. 7, 2000 (DE) .......................................... 100 60 754

(51) Int. Cl.⁷ .................................................. C07F 9/12
(52) U.S. Cl. ....................................................... 558/92
(58) Field of Search ........................................... 558/92

(56) References Cited

U.S. PATENT DOCUMENTS

| 3,174,931 A | * | 3/1965 | Matson et al. | |
| 5,281,741 A | | 1/1994 | Gunkel et al. | ................. 558/92 |
| 5,756,798 A | * | 5/1998 | Stults et al. | ................... 558/99 |
| 5,958,511 A | | 9/1999 | Dolan | ......................... 427/258 |

FOREIGN PATENT DOCUMENTS

| JP | 10-7689 | 1/1998 |
| JP | 10-17583 | 1/1998 |
| WO | 98/35970 | 8/1998 |
| WO | 99/55771 | 11/1999 |

* cited by examiner

Primary Examiner—Joseph K. McKane
Assistant Examiner—Kamal Saeed
(74) Attorney, Agent, or Firm—Joseph C. Gil; Diderico van Eyl

(57) ABSTRACT

The present invention relates to a process for preparing phosphoric acid esters, in particular a process for preparing monomeric bridged bisaryl diphosphates, wherein a water-binding agent is added to the reaction solution.

25 Claims, No Drawings

PROCESS FOR PREPARING PHOSPHORIC ACID ESTERS

The present invention relates to a process for preparing phosphoric acid esters, in particular a process for preparing monomeric bridged bisaryl diphosphates, wherein a water-binding agent is added to the reaction solution.

Bisaryl diphosphates, such as bisphenol A bis(diphenyl) phosphate and resorcinol bis(diphenyl)phosphate are known to be effective flame retardants for polymer resins. For example, a variety of polyphenylene oxide/high-impact polystyrene ("PPO/HIPS") and polycarbonate acrylonitrile-butadiene-styrene ("PC/ABS") blends can be improved with bisaryl diphosphate flame retardants.

When using bisaryl diphosphates to impart flame retardancy to plastics it is desired to use compounds having a high percentage of the monomer. This is because monomeric bisaryl diphosphates import beneficial physical properties to the polymer, which properties are not provided by their dimeric or polymeric counterparts. For example, resins to which monormeric bisaryl diphosphates have been added exhibit improved impact strength, melt flow index, tensile properties and flexural properties when compared to resins combined with dimeric or polymeric aryl phosphates.

Because of their commercial utility, various processes for the manufacture of monomeric bisaryl diphosphates have been developed. For example, it is known that bisphenol-A bis(diphenyl)phosphate can be obtained by catalytically reacting a phosphorus oxyhalide with bisphenol A (BPA) and then reacting the intermediate with phenol.

WO 99/55771 describes a process for continuously preparing monomeric bisaryl diphosphates, wherein no additional auxiliary agents are used in addition to the catalyst.

WO 98/47631 discloses a process for preparing aryl diphosphate esters, which comprises a third stage of filtering off he catalyst which is unsoluble in the reaction medium.

WO 98/35970 describes a semicontinuous process for preparing bisaryl diphosphates using magnesium chloride as a catalyst. The reaction product is not worked up here either.

EP 0 485 807 B1 describes a process for preparing aryl diphosphate esters in eight process steps, a workup or extraction of the catalyst being carried out in aqueous alkaline solution.

JP-A 10/017 583 discloses a batchwise synthesis for preparing phosphate ester oligomers, the reaction being controlled via the liberation rate of HCl gas. Excess phenol is removed by distillation. whereas the catalyst, for example magnesium chloride, is removed by washing.

Finally, JP-A 10/007 689 discloses a process for removing the metal chloride catalyst by means of an acidic aqueous solution (pH≦3) and at a temperature of at least 65° C.

A disadvantage of these processes is that water is introduced into the reaction system by the raw materials used, such as bisphenol A, resorcinol and phenol. The $POCl_3$ present is partially hydrolysed by water. This eventually leads to nonvolatile hydrolysis products which remain in the final product and damage the polymer during processing of the phosphates.

It is an object of the present invention to provide a process which produces oligophosphates comprising a significantly reduced proportion of hydrolysis products. It has now been found, surprisingly, that the addition of a water-binding agent to the reaction solution produces oligophosphates which comprise only small proportions of hydrolysis products.

The present invention therefore provides a process for the continuous, semicontinuous or batchwise preparation of phosphoric acid esters, characterized in that (1) a phosphorus oxyhalide is reacted with a polyol in the presence of a waterbinding agent to produce a monomeric halophosphate intermediate, and (2) the monomeric halophospate intermediate is reacted with an alcohol to produce the desired phosphoric acid ester.

In some preferred embodiments, the polyol in Step 1 is a dihydric alcohol, preferably bisphenol A or resorcinol, and that alcohol in Step 2 is a monohydric alcohol, preferably phenol. Conversely, in some preferred embodiments the phosphorus oxyhalide can also be reacted firstly with a monohydric alcohol to produce a monohalomonophosphoric acid diester intermediate. In some embodiments, the reaction of Step 1 and/or the reaction of Step 2 are carried out continuously. Particularly preferably, at least one step is carried out continuously or semicontinuously.

It is an object of the present invention to provide a method for continuously producing phosphoric acid esters using water-binding agents.

Another preferred object of the present invention is to provide a method for producing phosphoric acid esters in a (continuous reaction, wherein the monomeric halophosphate intermediate content of a reaction between phosphorus oxyhalide and a polyol is at least about 60%, preferably at least about 70% and particularly preferably at least about 80%.

The term continuous as used herein means that the reactants are fed into the apparatus at a constant flow rate and the reaction mixture is removed in an equally continuous manner. All reaction parameters are kept constant over time.

The term semicontinuous as used herein means that one reactant is introduced into the apparatus whereas another reactant is added slowly and continuously.

The term batchwise or discontinuously as used herein means that the reactants are introduced together into the apparatus, where they remain for a defined reaction time under set reaction conditions.

In a further preferred embodiment, Step 2 can be followed by a workup step 3 in which the product from Step 2 is worked up continuously, semicontinuously or batchwise in a phase separator at temperatures of 50 to 120° C.

The workup of Step 3 comprises both an acidic wash and an alkaline wash, which can likewise be operated in contiguous, semicontinuous or batchwise mode, preferably in continuous mode.

Any aqueous acid can be used foil the acidic wash, for example HCl, $H_2SO_4$, $H_3PO_4$, $CH_3COOH$. Particular preference is given to aqueous HCl, in particular in a concentration range from 0.5 to 10%. Any conventional basic salt can be used for the alkaline wash, for example NaOH, $Na_2CO_3$, $NaHCO_3$, sodium acetate and corresponding potassium salts. Particular preference is given to Na salts, in particular NaOH in a concentration range from 0.5 to 10%.

The process of the invention is particularly suitable for continuously preparing bisphenol A diphosphate (BDP) or resorcinol diphosphate (RDP), in which case the polyol used is resorcinol.

A further object of the invention is to provide a process for preparing monomeric phosphoric acid ester products which can be used as flame retardants, for example in plastics.

For the purposes of promoting al understanding of the principles of the invention, reference will now be made to preferred embodiments and specific language will be used to describe the same. It will nevertheless be understood that no limitation of the scope of the invention is thereby intended, such alterations and further modifications in the illustrated methods, and such further applications of the principles of the invention as illustrated therein, being contemplated as would normally occur to one skilled in the art to which the invention relates.

Preferably, the present invention relates generally to a continuous process for producing phosphoric acid esters, wherein at least one step is performed continuously, where a product can be produced which has a high monomeric halophosphate intermediate content relative to dimeric halophosphate intermediate content, along with high productivity, when the reaction is carried out in a continuous reactor system, such as a continuous stirred tank reactor (CSTR), using a dehydrating agent. The intermediate can be used, in certain embodiments, to form a desired monomeric phosphoric acid ester, including BPA bis(diphenyl) phosphate.

The preferred reactor design (i e., a continuous reactor) allows the production of product ratios otherwise unattainable in commercial quantities at high productivity.

The degree of oligomerization or polymerization can further be controlled to some extent by the degree of reaction completion in individual stages of a multiple stage continuous reactor series.

In one aspect of the invention, phosphoric acid esters are continuously produced by a two step process. In the first step, a content of at least about 60% monomeric halophosphate intermediate, preferably a bis(dichlorophosphate), is formed by continuously reacting a phosphorus oxyhalide with an alcohol, preferably a diol or other polyol. After preferably removing the excess phosphorus oxyhalide, the monomeric halophosphate intermediate is reacted with another alcohol, preferably a monohydric alcohol such as a phenol, to produce a desired phosphoric acid ester. The phosphorus oxyhalide, which has been removed for example by distillation, can be returned to the process, i.e. re-used for preparing the halophosphate intermediate.

The products of the Step 1 reaction are predominantly monomeric, and, as the monomeric product is used as a reactant in Step 2, the product of the Step 2 reaction will likewise be predominantly monomeric. However, it is recognized that, should one desire an oligomeric or polymeric component after forming the monomeric product from Step 1, the monomeric product from Step 1 may be reacted with a polyol in Step 2 and the resultant product may be further processed as desired.

In yet another aspect of the invention, the desired phosphoric acid esters are produced by continuously reacting phosphorous oxyhalide with a monohydric alcohol to produce a content of at least about 60% monohalomonophosphoric acid diester intermediate. The intermediate is then reacted with a polyol, preferably a dihydric alcohol, to produce the desired phosphoric acid ester.

Further describing one embodiment of the processes of the present invention, Step 1 of a process for preparing phosphoric acid esters preferably includes continuously reacting an appropriate alcohol with phosphorus oxyhalide in the presence of a Lewis acid catalyst. The phosphorus oxyhalide used in the present invention is generally of the formula $POX_n$ where X is a halide, including chloride or bromide, and n is preferably 3. Phosphorus oxychloride, $POCl_3$, is the most preferred phosphorus oxyhalide.

Step 1 produces a monomeric halophosphate intermediate when a polyhydric alcohol, such as a dihydric alcohol, is used. In that embodiment, the Step 1 reaction proceeds, diagrammatically, as follows:

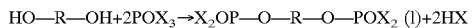
HO—R—OH+2POX$_3$→X$_2$OP—O—R—O—POX$_2$ (I)+2HX

Any unreacted $POX_3$ is removed by distillation under reduced pressure, leaving the Step 1 intermediate product I.

In the above diagram, R is the carbon chain portion (i.e. the aromatic, aliphatic, alicyclic portion or a combination thereof) of the alcohol, X is a halide as previously mentioned and compound I is the monomeric halophosphate intermediate product of Step 1.

Examples of appropriate alcohols include polyols, such as polyphenols, and including dihydric alcohols such as biphenols, bisphenol A, tetrabromobisphenol A, bisphenol S, bisphenol F, ethylene glycol, 1,4-butanediol, 1,2-hexanediol, resorcinol, catechol, hydroquinone and triflydric alcohols such as glycerol as well as other polyols. The aromatic and alicyclic portions of the alcohols may be alkyl- or halo-substituted. The aliphatic portion of the alcohol may also be halo-substituted. The alkyl substituent comprises saturated or unsaturated aliphatic hydrocarbon groups which may be either straight-chain or branched and have a carbon chain length of from 1 to 18. For example, the alkyl group includes methyl, ethyl and structural isomers of propyl, butyl, pentyl, hexyl, heptyl, octyl, nonyl, decyl, undecyl, dodecyl, tridecyl, tetradecyl, pentadecyl, iexadecyl, heptadecyl and octadecyl. The halo substituent is preferably chlorine and/or bromine. It is further preferred that there is no more than one substituent ortho to each hydroxyl group on an aromatic alcohol. The catalyst may be any Lewis acid (capable of promoting the reaction. Examples include, but are not limited to, $AlCl_3$, $ZnCl_2$, $CaCl_2$, $MgO$ or $MgCl_2$, preferably $MgO$ or $MgCl_2$.

The catalyst is used in an amount sufficient to allow the reaction to proceed smoothly and does not have to be removed from the final product. If it is desired to remove the catalyst as completely as possible from the product, the addition of Step 3 is recommended. The amount of catalyst used in Step 1 is typically in the range of about 100 ppm to about 5000 ppm (relative to the other reagents added to the first reactor), preferably 100 ppm to about 1000 ppm and most preferably about 300 ppm to about 700 ppm.

The reaction temperature in Step 1 will depend on the specific polyol reacted, but generally can be controlled over a wide range, from about 50° C. to about 250° C., and the process may be operated at atmospheric pressure, at a reduced pressure, or at an elevated pressure. However, a temperature of about 50° C. to about 200° C. is preferred, a temperature of about 80° C. to about 140° C. is particularly preferred, and a temperature of about 85° C. to about 100° C. in the first stage and second stage and about 100° C. to about 120° C. in subsequent stages is most preferred.

In the first step, the process may be operated with a sufficient excess of $POX_3$ to yield a workable reaction mass ac the reaction temperature, or an unreactive solvent may be used. The phosphorus oxyhalide/polyol mole ratio is typically about 2.5:1 to about 10:1, preferably about 3:1 to about 6:1 and most preferably about 4:1 to about 5:1. The residence time in each reactor may vary from 0.25 hours to about 6 hours.

After the reaction is complete, excess $POX_3$ is distilled off. This can be done both in the reactor and in suitable apparatuses, such as falling film or thin film evaporators. The distillation is carried out at a temperature of 80 to 200° C. and at a pressure of 10 to 100 mbar.

As mentioned above, the degree of oligomerization or polymerization can further be controlled to some extent by the degree of reaction completion in individual stages of a multiple stage continuous reactor series. The degree of reaction completion in Stage 1 of Step 1 is typically about 10 to about 100%, and about 20% to about 100% in subsequent stages. However, it is preferred that the degree of reaction completion in Stage 1 be about 30% to about 80% and in subsequent stages about 50% to about 100%. It is most preferred that the degree of reaction completion in Stage 1 be about 30% to about 50%, in Stage 2 about 70% to about 100% and in subsequent stages about 85% to about 100%.

The reaction of Step 1 is carried out by continuous or semicontinuous or batchwise reaction of the above-described reagents. As used herein, the term "continuously reacting" means that at least one stem, such as Step 1 or 2 or, if desired, Step 3, can be carried out at least partly continuously (i.e. the step can be divided into various stages and at least one stage is carried out continuously) or the entire step can be carried out continuously. The number of stages may range from about 1 to about 5, preferably from about 1 to about 3 and most preferably from about 2 to about 3.

However, it is also possible to carry out Step 1 in continuous or semicontinuous mode and Step 2 in batchwise mode. Alternatively, it is also possible to carry out only Step 2 in continuous or semicontinuous mode and Step 1 in batchwise mode.

It is likewise possible to use any combination of continuous, semicontinuous or batchwise operation of the individual steps, including batchwise operation of all Steps 1, 2 and, if desired, 3.

The term "continuous reactor" as used herein refers to a vessel where raw materials or a feed stream containing unreacted or partially reacted material is added continuously or essentially continuously while material is being removed from the vessel to maintain an essentially constant reactor volume, and where conditions in the vessel are such that a finite degree of reaction occurs.

As indicated above, the selection of reactor design to accomplish the continuous portion of the reaction in either Step 1 or Step 2 plays an important role in determining the degree of oligomerization or polymerization and the quality of the product. Examples of commercially available reactors that might be used to practice the invention, and that one skilled in the art is familiar with, include falling film or thin film reactors, continuously stirred tank reactors (CSTRs), tube reactors and packed column reactors. Although a wide variety of reactors may be used to practice the invention, CSTRs are preferred.

A series of continuous reactors may employ the same type, or a different type, of reactor. It is further preferred that a CSTR be used in Stage 1 of a step and then either another CSTR may be used or a batch reactor may be used. It is most preferred to use a series of CSTRs or, alternatively, a series of CSTRs, the final stage being carried out in a batch reactor.

It is noted that, along with the monomeric product produced in the Step 1 reaction diagrammed above, dimeric, other oligomeric or polymeric products may be formed. For example, referring to the diagram of the Step 1 reaction above, compound I may react with Step 1 reactants (i.e., with the dihydric alcohol and POX$_3$) to form the following dimeric component:

X$_2$OP—O—R—O—POX—O—R—O—POX$_2$

The above dimeric component may also be produced by reaction of the following reactants and intermediates from the reaction of Step 1:

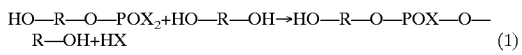

HO—R—O—POX$_2$+HO—R—OH→HO—R—O—POX—O—R—OH+HX  (1)

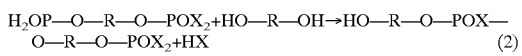

H$_2$OP—O—R—O—POX$_2$+HO—R—OH→HO—R—O—POX—O—R—O—POX$_2$+HX  (2)

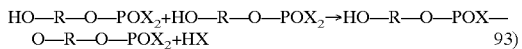

HO—R—O—POX$_2$+HO—R—O—POX$_2$→HO—R—O—POX—O—R—O—POX$_2$+HX  (3)

It is obvious that the product formed from (1)–(3) above must be further reacted with POX$_3$ to form the dimeric component.

A suitable method for determining the relative amounts of monomer, dimer and further homologues of Step 1 is liquid chromatography (GPC) using an RI detector.

The reaction of Step 1 preferably forms a content of at least about 60% monomeric halophosphate intermediate. It is further preferred that the reaction of Step 1 forms a content of at least about 70%, particularly preferably at least about 80%, monomeric halophosphate intermediate.

Referring now to Step 2 of the process, the product of Step 1 is reacted with an alcohol, such as a monohydric alcohol including phenol, in a similar way using a Lewis acid catalyst. In one embodiment, Step 2 may be depicted diagrammatically as follows:

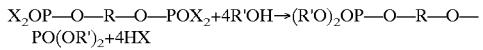

X$_2$OP—O—R—O—POX$_2$+4R'OH→(R'O)$_2$OP—O—R—O—PO(OR')$_2$+4HX

X and R are as defined above for Step 1 and X$_2$OP—O—R—O—POX$_2$ is a monomeric halophosphate intermediate. R'OH is the monohydric alcohol, R' being the carbon chain portion (i.e., the aromatic, aliphatic, alicyclic, portion or a combination thereof) of the alcohol, and (R'O)$_2$OP—O—R—O—PO(OR')$_2$ is the desired phosphoric acid ester product. When R'OH includes an aromatic or alicyclic ring, the aromatic or alicyclic ring may be alkyl- or halo-substituted as discussed above for the dihydric alcohol in Step 1. The aliphatic portion of the alcohol may also be halo-substituted as discussed above. It is further preferred that there is no more than one substituent ortho to each hydroxyl group on an aromatic alcohol. Examples of the alcohol that may be reacted in Step 2 include, but are not limited to, phenol, xylenols, tribromophenol, methanol, t-butanol, cyclohexanol and phenol/formaldehyde condensates. It is preferred to carry out Step 2 by reacting the halophosphate intermediate product of Step 1 with phenol using magnesium chloride as a catalyst.

As in the first step, the phenol (or other alcohol) and the product of Step 1 can be continuously fed to a CSTR in Step 2. Alternatively, the phenol (or other alcohol) can be added as a single charge to the product of Step 1, and the resulting mixture can be fed continuously to the reactor.

The discharge from the first continuous reactor may be fed to a second continuous reactor where the material is held at 125–250° C. for a residence time of about 0.25–6 hours. The total phenol charge may be added to the first reactor or split such that part of the total phenol charge is added to the first reactor and the remainder added to the second reactor.

The discharge from the second reactor is fed to a buffer tank. The buffer tank is used to feed a continuous or batch vacuum stripper adapted to remove excess alcohol from Step 2, such as phenol. The alcohol, for example phenol, excess which has been removed can be returned to the process, i.e. reused for carrying out Step 2. A catalyst is used as in the reaction of Step 1.

The reaction of Step 2 is typically performed at a temperature sufficient to convert the halophosphate intermediate to the desired phosphoric acid ester product. Although this temperature may vary depending on the reagents used and the desired product, the temperature of the material in the reactor advantageously ranges from 50° C. to about 250° C., but preferably from about 125° C. to about 250° C. The volume of the reactor is preferably adjusted so that the residence time ranges from about 0.25 to 6 hours.

The alcohol/monomeric halophosphate intermediate mole ratio is typically about 4:1 to about 5:1, but preferably abort 4.04:1 to about 4.40:1, and most preferably about 4.04:1 to about 4.12:1. As in the first step, an excess of the alcohol may be used to improve the ease of processing, or an unreactive solvent may be employed. Any excess of alcohol is removed subsequent to Step 2 under reduced pressure, which can likewise be done continuously or batchwise.

In a preferred embodiment of the first aspect of the invention, BPA is continuously added to magnesium chloride and phosphorus oxychloride in a dissolution vessel at a temperature of about 50° C. The relative feed rates are such that the phosphorous oxychloride/BPA mole ratio is about 5:1. The reaction mixture is then fed to a first CSTR at a temperature of about 90° C. The volume of the reactor is maintained to give a residence time of about 1 hour.

The contents of the first reactor are continuously removed and transferred to further CSTRs arranged in series, successively increasing the temperature to about 100° C. and finally 120° C. The feed and discharge rates from the reactor are such that the residence time is about 1 hour in each case.

The discharge from the last reactor is fed to a buffer tank, which is maintained at about 90° C. while being filled. The filled buffer tank is used to feed a continuous distillation to remove the excess POCl$_3$ from the product of Step 1.

The product of Step 1 is then reacted with phenol using magnesium chloride as a catalyst.

As briefly mentioned above, the inventive continuous process may be operated such that part of the first step or second step is performed in a continuous reactor with the rest of the reaction being completed in a batchwise reactor or reactors. Similarly, an entire step may be performed in a continuous reactor or series of continuous reactors, while the other step is carried out in batch reactors. The steps may be carried out so as to maximize production of monomeric halophosphate intermediate product and, consequently, monomeric phosphoric acid ester product.

The monomer content of the reaction product of Step 2 depends on the presence of a high percentage of monomeric halophosphate intermediate which acts as a reactant in Step 2. Thus, if a large amount of monomeric halophosphate intermediate is produced in Step 1 relative to the (dimeric component, the monomer content of the reaction of Step 2 will also be relatively large. That is, relatively large amounts of the monomeric phosphoric acid ester product of Step 2 will be formed compared to dimeric, oligomeric or polymeric phosphoric acid ester product.

Parameters that can affect the properties and quality of the products of Step 1 and Step 2 include catalyst selection and amount of catalyst used, and phosphorus oxyhalide/alcohol ratio. Each of these parameters has an optimum range to give a flame retardant material exhibiting the desired properties. In addition, the moisture content of each starting material has an effect on the final product quality. For example, if the moisture content of the reactants is kept low, a larger amount of monomeric product can be obtained.

When Step 1 or Step 2 are performed in a series of reactors, at least one of which is a continuous reactor, the raw materials, such as solvent, catalyst, phosphorus oxyhalide, alcohol (i.e. phenol or polyol, such as a diol) may be added to just the first reactor in the series or to downstream reactors in addition to the first. This can be done to improve the ease of processing, to control product quality and/or to obtain the desired product or mixture of products.

Water removal agents used may be both physical and chemical agents, such as zeolites, PCl$_5$, P$_4$O$_{10}$, silica gel, water-binding salts, magnesium alkyls and other organometallic compounds or other substances known to the person skilled in the art to have a water-binding effect. These agents are used in a sufficent amount to remove the water introduced by the starling materials. The required amount depends on the type of water-binding agent used. A typical amount to be used is from 0.1 to 5% (based on the sum of the starting materials). These water-binding agents can be added in Step 1 and/or Step 2 of the reaction. It is furthermore possible to generate the water-binding agent in situ in one of the reagents, for example by converting PCl$_3$ to from PCl$_5$ by chlorination.

In an alternative embodiment, a process for preparing phosphoric acid esters is provided which is characterized in that (1) a phosphorus oxyhalide is reacted continuously, semi-continuously or batchwise with a monohydric alcohol in the presence of a dehydrating agent to produce a monohalomonophosphoric acid diester intermediate, and (2) said monohalomonophosphoric acid diester intermediate is reacted continuously, semicontinuously or batchwise with a polyol to produce the desired phosphoric acid ester.

This process is followed, if desired, by an additional workup step in which the product from Step 2 is worked up continuously, semicontinuously or batchwise in a phase separator at temperatures of 50 to 120° C., preferably 70 to 90° C.

In this second aspect of the invention, the products from this step are then reacted with the chosen alcohol selected from the alcohols described above, preferably a polyol, such as a diol, to give the desired phosphoric acid ester. This route also utilizes Lewis acid catalysts, water-binding agents and continuous addition of reactants as described for the other embodiments. Step 2 product composition and properties are similar to those obtained in the previously described route. The inventive continuous process may be operated in a similar fashion as described above. For example, in certain embodiments the reaction of the intermediate with the polyol may also be performed in a continuous reactor. Alternatively, the first reaction may be performed in a batch reactor and the second reaction may be performed continuously.

Referring more specifically to the above alternative embodiment, the Step 1 reaction of the monohydric alcohol with the phosphorus oxyhalide may be diagrammed as follows:

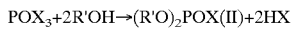

POX$_3$+2R'OH→(R'O)$_2$POX(II)+2HX

R'OH and X are as previously defined and compound II is the monohalomonophosphoric acid diester intermediate.

The specific catalyst and the quantify used are the same as in the previous embodiments discussed. The same applies to the type and quantity of the water-binding agents.

The reaction temperature in Step 1 of the alternative embodiment can likewise be controlled over a wide range, from about 50° C. to about 250° C., and the process may similarly be operated under various pressures. However, a temperature of 50° C. to about 200° C. is preferred, and a temperature of about 90° C. to about 140° C. is particularly preferred. Moreover, residence times are typically about 0.25 hours to about 6 hours.

The alcohol/phosphorus oxyhalide mole ratio is advantageously from about 1.5:1 to about 3:1, and particularly preferably from about 1.75:1 to about 2.25:1.

Reaction of phosphorus oxyhalide with a monohydric alcohol may yield the following undesired compounds:

| | |
|---|---|
| (R'O)POX$_2$ | (III) |
| (R'O)$_3$PO | (IV) |

Compound III is a dihalomonophosphoric acid monoester intermediate and Compound IV is a phosphoric acid triester. Compound IV is undesired as this compound can no longer react with a polyol in Step 2 to produce a desired phosphoric acid ester product. Compound III is undesired because it has the potential of reacting with the reactants and intermediates formed in the reaction of Step 2, and can thus lead to formation of dimeric, oligomeric or polymeric products in Step 2. As one skilled in the art is aware of the specific undesired reactions that may proceed and products that may be produced, it is not necessary to describe them here.

The reaction between phosphorus oxyhalide and the monohydric alcohol will typically produce a content of at least about 60% monohalomonophosphoric acid diester.

It is further preferred that at least about 70%, particularly preferably at least about 80%, of the monohalomonophosphate diester is produced.

Step 2 of the alternative embodiment may be diagrammed as follows:

2(R'O)$_2$POX+HO—R—OH→(R'O)$_2$OP—O—R—PO(OR')$_2$+2HX

R' and X are as defined above. The reaction of Step 2 produces the desired monomeric phosphoric acid ester product, (R'O)$_2$OP—O—R—O—PO(OR')$_2$.

The specific catalyst and the quantity used is the same as in the embodiments discussed previously. The same applies to the type and quantity of the water-binding agents.

The reaction temperature in Step 2 of the alternative embodiment can also be controlled over a wide range, from about 50° C. to about 250° C., and the process may similarly be operated under various pressures. However, a temperature of about 125° C. to about 250° C. is preferred. Moreover, residence times are typically about 0.25 hours to about 6 hours.

The polyol/monohalomonophosphoric diester intermediate mole ratio is advantageously from about 0.3:1 to about 0.8:1, and particularly preferably from about 0.4:1 to about 0.6:1. The preferred degrees of reaction completion in Step 1 are similar to those described above.

The phosphoric acid esters prepared by the methods of the present invention can be utilized as flame retardants in resin compositions. The resin may be a polymer and may include polyphenylene oxide, high-impact polystyrene, polycarbonate, polyurethane, polyvinyl chloride, acrylonitrile-butadiene-styrene, polybutylene terephthalate and mixtures thereof. A wide variety of other polymer resins may also be used.

The examples which follow illustrate the invention. The resulting bisaryl phosphate is characterized with regard to it, hydrolysis products. The hydrolysis products are determined by liquid chromatography (reverse phase HPLC) using a UV detector at 254 nm. The hydrolysis products are specified as the sum of the individual products.

EXAMPLE 1 (BATCHWISE PREPARATION OF BDP)

Step 1

537 g (3.5 mol) of phosphorus oxychloride and 228 g (1.0 mol) of bisphenol A are introduced together into a dry apparatus which has been flushed with nitrogen and and consists of a 1l four-neck flask, paddle stirrer, thermometer and jacketed coil condenser with bubbler. 0.67 g (7 mmol) of magnesium chloride catalyst are added. The temperature is raised to 130° C. with stirring. HCl evolution commences between 100 and 105° C. The HCl eliminated during the reaction is absorbed in a gas-washing bottle filled with water. As soon as the HCl evolution ceases, a gentle stream of nitrogen is passed through the apparatus to drive off any redisual HCl. The amount of HCl absorbed is determined by weighing the gas-washing bottle. Amount of HCl: about 73 g.

A distillation head is then fitted to the apparatus, and excess phosphorus oxychloride is distilled off at atmospheric pressure and at a temperature of 130 to 150° C. The pressure is then reduced to 85 mbar to distill off any residual phosphorus oxychloride.

Step 2

The reaction mixture is cooled to about 100° C. at atmospheric pressure, then admixed with 370 g (3.94 mol) of phenol and reheated. HCl evolution recommences between 120 and 130° C. The internal temperature is raised to 200° C. in a plurality of stages in the course of about 4 hours. The hydrochloric acid is again absorbed in water. When the final temperature is reached, nitrogen is bubbled through the reaction mixture for 1 hour. Amount of HCl: about 141 g.

The results are summarized in the Table below.

EXAMPLES 2 to 5

The experiments are carried out is described in Example 1, except that phosphorus pentachloride was added to the reaction mixture (cf. Table).

| | Example 1 | Example 2 | Example 3 | Example 4 | Example 5 |
|---|---|---|---|---|---|
| POCl$_3$/BPA | 3.5 | 3.5 | 3.5 | 3.5 | 3.5 |
| Addition of PCl$_5$ | | | | | |
| Step 1 mmol | — | 7 | — | 7 | 14 |
| Step 2 mmol | — | — | 7 | 7 | — |
| Hydrolysis products % | 1.31 | 0.68 | 0.76 | 0.09 | 0.25 |

It can be seen that the amount a f hydrolysis products is significantly reduced by the addtion of PCl$_5$.

EXAMPLE 6 (CONTINUOUS PREPARATION OF BDP)

Experiments were conducted in a tank battery consisting of 4 one-liter reactors equipped with a stirrer, reflux condenser, thermocouple, and heating mantle. The reaction mixture is kept constant at 1l by means of an overflow. The reaction temperature is set for each reactor via a separate thermostat.

Step 1

The reaction mixture (POCl$_3$/BPA mole ratio=5.0, MgCl$_2$ 7 mmol/mol BPA) is introduced into a receptacle at 50° C. and transferred to the first reactor by means of a pump. Hydrochloric acid liberated in the reaction is vented and absorbed in water. The following temperature profile is set for the tank battery 82/86/105/120° C. The flow rate is 1.5–2.0 l/h, resulting in an average residence time of 2–2.5 h.

After the reaction, excess $POCl_3$ is continuously distilled off and returned to the reaction.

Step 2

The intermediate from Step 1 is introduced into the receptacle and admixed with the desired amount of phenol at 50° C. (8 mol% excess based on the Cl content of the intermediate). The reaction mixture is transferred to the first reactor by means of a pump. The following temperature profile is set: 135/160/190/210° C. The flow rate is 1.0–1.3 l/h. The average residence time is 3–4 hours.

After the reaction, excess phenol is continuously distilled off and returned to the reaction.

Samples are taken every 4 hours, beginning 12 hours after the start of the reaction. The results are given in the Table below and are in each case averages of 4 consecutive samples.

EXAMPLES 7 TO 9

The procedure described in Example 6 is repeated. For the reaction of Stage 1, varying amounts of $PCl_5$ are introduced into the receptacle (reaction mixture). The results are summarized in the Table below.

|  | Example 6 | Example 7 | Example 8 | Example 9 |
|---|---|---|---|---|
| $POCl_3$/BPA | 5.0 | 5.0 | 5.0 | 5.0 |
| Addition of $PCl_5$ |  |  |  |  |
| Step 1 mmol | — | 7 | 14 | 21 |
| Step 2 mmol | — | — | — | — |
| Hydrolysis products % | 2.0 | 0.91 | 0.23 | 0.08 |

The examples shown indicate that the continuous reaction in the presence of $PCl_5$ likewise produces oligophosphates comprising <1% of hydrolysis products.

What is claimed is:

1. A process for the continuous or batchwise preparation of phosphoricacid esters comprising:
   (1) reacting a phosphorus oxyhalide with a polyol in the presence of a water-binding agent to produce a monomeric halophosphate intermediate, and
   (2) reacting the monomeric halophosphate intermediate with an alcohol to produce the desired phosphoric acid ester.

2. The process according to claim 1, wherein said reaction of a phosphorus oxyhalide with a polyol is carried out at temperatures of about 50 to about 250° C.

3. The process according to claim 1, wherein the reaction of a phosphorus oxyhalide with a polyol is carried out in the presence of a catalyst.

4. The process according to claim 3, wherein said catalyst is a Lewis acid.

5. The process according to claim 4, wherein said Lewis acid is MgO or $MgCl_2$.

6. The process according to claim 1, wherein the reaction of said monomeric halophosphate intermediate with an alcohol is carried out continuously.

7. The process according to claim 1, wherein said phosphorusoxyhalide is phosphorus oxychloride.

8. The process according to claim 1, wherein said dihydric alcohol is bisphenol A or resorcinol.

9. The process according to claim 1, wherein said alcohol is phenol.

10. The process according no claim 1, wherein said monomeric halophosphate intermediate is a diphosphorotetrahalidate.

11. The process according to claim 1, wherein the water-binding agent is a physical agent or a chemical agent.

12. The process according to claim 1, wherein zeolites or $PCl_5$ are used as dehydrating agents.

13. The process according to claim 1, wherein the process further comprises a workup step.

14. A process for the continuous or batchwise preparation of phosphoric acid esters comprising
   (1) reacting a phosphorus oxyhalide with a polyol in the presence of $PCl_5$ to produce a monomeric halophosphate intermediate, and
   (2) reacting the monomeric halophosphate intermediate with an alcohol to produce the desired phosphoric acid ester.

15. The process according to claim 14, wherein said reaction of a phosphorus oxyhalide with a polyol is carried out at temperatures of about 50 to about 250° C.

16. The process according to claim 14, wherein the reaction of a phosphorus oxyhalide with a polyol is carried out in the presence of a catalyst.

17. The process according to claim 16, wherein said catalyst is a Lewis acid.

18. The process according to claim 17, wherein said Lewis acid is MgO or $MgCl_2$.

19. The process according to claim 14, wherein said reaction of said monomeric halophosphate intermediate with an alcohol is carried out continuously.

20. The process according to claim 14, wherein said phosphorus oxyhalide is phosphorus oxychloride.

21. The process according to claim 14, wherein said dihydric alcohol is bisphenol A or resorcinol.

22. The process according to claim 14, wherein said alcohol is phenol.

23. The process according to claim 14, wherein said monomeric halophosphate intermediate is a diphosphorotetrahalidate.

24. The process according to claim 14, wherein the dehydrating agent is a physical or chemical agent.

25. The process according to claim 14, wherein the process further comprises a workup step.

* * * * *